US010335389B2

(12) United States Patent
Kawakami et al.

(10) Patent No.: US 10,335,389 B2
(45) Date of Patent: Jul. 2, 2019

(54) BERAPROST-CONTAINING PATCH

(71) Applicant: TEIKOKU SEIYAKU CO., LTD., Kagawa (JP)

(72) Inventors: Satoshi Kawakami, Sanuki (JP); Manabu Sogabe, Awa (JP); Taiki Shibata, Higashikagawa (JP)

(73) Assignee: TEIKOKU SEIYAKU CO., LTD., Kagawa (JP)

( * ) Notice: Subject to any disclaimer, the term of this patent is extended or adjusted under 35 U.S.C. 154(b) by 114 days.

(21) Appl. No.: 14/910,738

(22) PCT Filed: Aug. 7, 2014

(86) PCT No.: PCT/JP2014/070899
§ 371 (c)(1),
(2) Date: Feb. 8, 2016

(87) PCT Pub. No.: WO2015/020153
PCT Pub. Date: Feb. 12, 2015

(65) Prior Publication Data
US 2016/0193178 A1 Jul. 7, 2016

(30) Foreign Application Priority Data
Aug. 9, 2013 (JP) ................................. 2013-166302

(51) Int. Cl.
A61K 31/343 (2006.01)
A61K 47/10 (2017.01)
A61K 31/5585 (2006.01)
A61K 47/02 (2006.01)
A61K 47/12 (2006.01)
A61K 9/70 (2006.01)

(52) U.S. Cl.
CPC .......... *A61K 31/343* (2013.01); *A61K 9/7053* (2013.01); *A61K 9/7061* (2013.01); *A61K 9/7069* (2013.01); *A61K 31/5585* (2013.01); *A61K 47/02* (2013.01); *A61K 47/10* (2013.01); *A61K 47/12* (2013.01)

(58) Field of Classification Search
CPC .................................................... A61K 31/343
USPC ........................................................ 514/468
See application file for complete search history.

(56) References Cited

U.S. PATENT DOCUMENTS

| 5,854,281 A | 12/1998 | Uekama et al. |
| 7,553,867 B2 * | 6/2009 | Hamamura .......... C07D 307/38 514/438 |
| 2004/0202706 A1 | 10/2004 | Koo et al. |
| 2005/0266062 A1 | 12/2005 | Mori et al. |
| 2007/0148217 A1 | 6/2007 | Mori et al. |
| 2010/0119584 A1 | 5/2010 | Matsuzawa et al. |
| 2012/0220962 A1 * | 8/2012 | Hsu ..................... A61K 9/0014 604/307 |
| 2013/0005817 A1 | 1/2013 | Tani |
| 2014/0275237 A1 * | 9/2014 | Faulds ............... A61K 31/7012 514/468 |

FOREIGN PATENT DOCUMENTS

| JP | 2006-517224 | 7/2006 |
| JP | 2013-67584 | 4/2013 |
| WO | 96/15793 | 5/1996 |
| WO | 2004/041270 | 5/2004 |
| WO | 2005/046680 | 5/2005 |
| WO | 2008/146796 | 12/2008 |
| WO | 2011/111809 | 9/2011 |

OTHER PUBLICATIONS

Extended European Search Report dated Mar. 17, 2017 in corresponding European Application No. 14835157.0.
Prausnitz et al., "Transdermal Drug Delivery", Nature Biotechnology, vol. 26, No. 11, (2008), pp. 1261-1268.
International Search Report dated Oct. 21, 2014 in International Application No. PCT/JP2014/070899.
International Preliminary Report on Patentability dated Feb. 9, 2016 in International Application No. PCT/JP2014/070899.
Machine translation of JP 2013-67584 cited in an IDS filed on Feb. 8, 2016.

* cited by examiner

Primary Examiner — Jennifer M Kim
(74) Attorney, Agent, or Firm — Wenderoth, Lind & Ponack, L.L.P.

(57) ABSTRACT

The present invention provides a patch containing beraprost or a pharmacologically acceptable salt thereof, which achieves high transdermal absorption of beraprost or a pharmacologically acceptable salt thereof and has excellent formulation properties.

6 Claims, No Drawings

BERAPROST-CONTAINING PATCH

TECHNICAL FIELD

The present invention relates to a patch comprising beraprost or a pharmacologically acceptable salt thereof, which achieves high transdermal absorption of beraprost or a pharmacologically acceptable salt thereof and has excellent formulation properties.

BACKGROUND ART

Beraprost sodium is a prostacyclin (PGI2) derivative having a vasodilating action and a platelet aggregation inhibition action, which is used for improving ulcer, pain, and coldness associated with arteriosclerosis obliterans or thromboangiitis obliterans and widely distributed in the market as an oral formulation. However, an oral administration of the drug rapidly elevates its blood level and causes side effects such as facial flushing, hot flash, headache dull, and anorexia.

Recently, a patch draws attention as a formulation for administering the drug in a body in the light of ease in handling or dosage management. Such a transdermal absorption-type formulation is expected to suppress the rapid elevation of the blood level, maintain the stable blood level, and thus reduce the side effects.

Generally, transdermal absorption-type formulations can be classified into the following types.

(1) an oily patch, which is prepared by adding an active ingredient to an adhesive base (an oily base) comprising a water-insoluble natural or synthetic polymer compound such as a resin, a plastic, and a rubber as the main base, a softener, a tackifier resin, and optionally other ingredients, followed by homogeneously stirring the obtained mixture, and then spreading it on or enclosing it in a fabric or a plastic film to form a patch;

(2) an aqueous patch, which is prepared by mixing and kneading a natural or synthetic polymer compound such as a water-soluble polymer and a water-absorbing polymer, other ingredients such as glycerin, and purified water (hereinafter also referred to as "water"), followed by adding an active ingredient to the obtained mixture and homogeneously stirring it, and then spreading it on a backing or a liner such as a fabric to form a patch; and (3) a non-aqueous patch, which is prepared by mixing and kneading ingredients such as polyacrylic acid and a polyhydric alcohol, followed by adding an active ingredient to the obtained mixture and homogeneously stirring it, and then spreading it on a backing or a liner such as a fabric to form a substantially water-free patch.

Beraprost or a pharmacologically acceptable salt thereof has been mainly and variously developed as an oily patch until now. For example, Patent Document 1 discloses an oily patch comprising beraprost and saturated fatty acid or unsaturated fatty acid and Patent Document 2 discloses an oily patch comprising this drug and a fatty alcohol having 14 to 20 carbon atoms as an absorption enhancer. However, the affinity of beraprost for an oily base in an oily patch becomes too high, and desired transdermal absorption cannot be achieved. Further, if an absorption enhancer is added to an oily patch to improve the transdermal absorption of the drug, the formulation properties become worse.

CITATION LIST

Patent Documents

Patent Document 1: WO1996/015793A1
Patent Document 2: JP2013-67584A

SUMMARY OF INVENTION

Problems to be Solved by the Invention

The present invention has been made in view of the above problems in the background art, and provides a patch which achieves high transdermal absorption of beraprost or a pharmacologically acceptable salt thereof and has excellent formulation properties.

Means for Solving the Problems

The present inventors have studied earnestly in order to solve the above problems, and especially studied an adhesive base for use in a patch comprising beraprost or a pharmacologically acceptable salt thereof. As a result, the present inventors have found that a patch which achieves significantly elevated transdermal absorption of beraprost and has excellent formulation properties can be obtained when beraprost or a pharmacologically acceptable salt thereof is added to an adhesive base comprising a water-soluble polymer, a polyhydric alcohol, and a cross-linking agent, and finally completed the present invention.

Namely, the present invention relates to (1) A patch comprising beraprost or a pharmacologically acceptable salt thereof, a water-soluble polymer, a polyhydric alcohol, and a cross-linking agent;

(2) The patch according to the above item (1), comprising 0.01 to 10% by weight of the beraprost or a pharmacologically acceptable salt thereof, 1 to 30% by weight of the water-soluble polymer, 5 to 95% by weight of the polyhydric alcohol, and 0.01 to 5% by weight of the cross-linking agent to the weight of a pasty preparation;

(3) The patch according to the above item (1) or (2), wherein the beraprost or a pharmacologically acceptable salt thereof is beraprost sodium;

(4) The patch according to any one of the above items (1) to (3), wherein the water-soluble polymer is one or more water-soluble polymers selected from the group consisting of polyacrylic acid, polyacrylic acid salt, partially neutralized polyacrylic acid, carmellose sodium, polyvinyl alcohol, hydroxyethylcellulose, hydroxypropylcellulose, and carboxyvinyl polymer;

(5) The patch according to any one of the above items (1) to (4), wherein the polyhydric alcohol is one or more polyhydric alcohols selected from the group consisting of propylene glycol, glycerin, D-sorbitol, and 1,3-butylene glycol; and (6) The patch according to any one of the above items (1) to (5), wherein the cross-linking agent is one or two cross-linking agents selected from the group consisting of aluminum glycinate and magnesium aluminometasilicate.

Effect of the Invention

According to the present invention, a patch which achieves high skin permeability of beraprost or a pharmacologically acceptable salt thereof and has excellent formulation properties can be provided by preparing a patch comprising beraprost or a pharmacologically acceptable salt thereof, a water-soluble polymer, a polyhydric alcohol, and a cross-linking agent.

DESCRIPTION OF EMBODIMENTS

Beraprost in a patch of the present invention may be in the free form or a salt form, and a salt form is preferable. Examples of the salt form of beraprost include aluminum salt, amine salt, and sodium salt, and sodium salt (i.e., beraprost sodium) is especially preferable. Also, the amount of beraprost or a pharmacologically acceptable salt thereof in the patch of the present invention is not limited to a specific amount as long as it has a therapeutic effect, and may be 0.01 to 10% by weight, preferably 0.2 to 4% by weight, more preferably 0.5 to 2% by weight to the weight of a pasty preparation. When the amount of beraprost or a pharmacologically acceptable salt thereof is less than 0.01% by weight, sufficiently high transdermal absorption of the drug cannot be achieved. Meanwhile, when the amount of beraprost or a pharmacologically acceptable salt thereof is more than 10% by weight, the cost effectiveness is not preferable.

Examples of the water-soluble polymer used in the patch of the present invention include polyacrylic acid, polyacrylic acid salt, partially neutralized polyacrylic acid, carmellose sodium, carboxyvinyl polymer, gelatin, methyl vinyl ether-maleic anhydride copolymer, N-vinylacetamide copolymer, sodium alginate, polyvinyl alcohol, polyvinylpyrrolidone, polyvinyl methacrylate, polyethylene oxide, carboxyvinyl polymer, carboxymethylcellulose, hydroxymethylcellulose, hydroxyethylcellulose, hydroxypropylcellulose, methylcellulose, ethylcellulose, starch-acrylic acid graft copolymer, carrageenan, sodium alginate, agar, acacia gum, guar gum, xanthan gum, gum arabic, karaya gum, tragacanth gum, and collagen, and they may be used alone or in a combination of two or more of them. Especially, one or more water-soluble polymers selected from the group consisting of polyacrylic acid, polyacrylic acid salt, partially neutralized polyacrylic acid, carmellose sodium, polyvinyl alcohol, hydroxyethylcellulose, hydroxypropylcellulose, and carboxyvinyl polymer are preferably used.

Meanwhile, a non-aqueous patch of the present invention which does not comprise water in a pasty preparation preferably comprises polyacrylic acid as the water-soluble polymer. More preferably, said polyacrylic acid used in the non-aqueous patch has a viscosity of 5000 to 150000 (cps/25° C.) in its 10% by weight aqueous solution.

The amount of water-soluble polymer is 1 to 30% by weight, preferably 5 to 25% by weight, more preferably 9 to 20% by weight to the weight of a pasty preparation. When the amount of water-soluble polymer is less than 1% by weight, the gel in the pasty preparation is not sufficiently solidified. Meanwhile, when the amount is more than 30% by weight, the gel in the pasty preparation becomes too hard and causes problems such as undesired adhesiveness and inefficient workability in the manufacturing process.

The polyhydric alcohol used in the present invention acts as a solubilizer of the water-soluble polymer, and also as a transdermal absorption enhancer which promotes the skin permeability of beraprost by producing a water-holding effect on a skin. Examples of the polyhydric alcohol include ethylene glycol, propylene glycol, polyethylene glycol, polypropylene glycol, 1,3-butylene glycol, glycerin, and D-sorbitol, and they may be used alone or in a combination of two or more of them. Especially, one or more polyhydric alcohols selected from the group consisting of propylene glycol, glycerin, D-sorbitol, and 1,3-butylene glycol are preferably used.

The amount of polyhydric alcohol used in the patch of the present invention is 5 to 95% by weight to the weight of a pasty preparation. An aqueous patch comprising water in the pasty preparation preferably comprises 20 to 80% by weight, and more preferably comprises 20 to 60% by weight of the polyhydric alcohol. Meanwhile, a non-aqueous patch preferably comprises 50 to 95% by weight, and more preferably comprises 55 to 90% by weight of the polyhydric alcohol. When the amount of polyhydric alcohol is less than 5% by weight, ingredients such as water-soluble polymer are not sufficiently dissolved in the pasty preparation and the absorption of the drug decreases. Meanwhile, when the amount of polyhydric alcohol is more than 95% by weight, the formulation properties becomes worse.

Examples of the cross-linking agent used in the patch of the present invention include, but is not limited to, various polyvalent metal salts and an organic cross-linking agent such as dialdehyde starch. Especially, a polyvalent metal salt is preferably used. Examples of the polyvalent metal salt as the cross-linking agent include magnesium chloride, calcium chloride, aluminum chloride, magnesium oxide, calcium oxide, aluminum oxide, potassium alum, magnesium hydroxide, calcium hydroxide, aluminum hydroxide, calcium carbonate, magnesium carbonate, dried aluminum hydroxide gel, calcium phosphate, magnesium phosphate, aluminum phosphate, calcium citrate, aluminum acetate, aluminum glycinate, hydrous aluminum silicate, magnesium aluminometasilicate, aluminum lactate, and synthetic hydrotalcite, and they may be used alone or in a combination of two or more of them. One or two cross-linking agents selected from the group consisting of aluminum glycinate and magnesium aluminometasilicate are preferably used.

The amount of cross-linking agent is 0.01 to 5% by weight, preferably 0.05 to 3% by weight, more preferably 0.1 to 2.5% by weight to the weight of a pasty preparation. When the amount of cross-linking agent is less than 0.01% by weight, the gel in the pasty preparation is not sufficiently cross-linked. Meanwhile, when the amount of cross-linking agent is more than 5% by weight, the gel in the pasty preparation becomes too hard.

One preferable embodiment of the present invention provides a patch, wherein the beraprost or a pharmacologically acceptable salt thereof is beraprost sodium, the water-soluble polymer is one or more water-soluble polymers selected from the group consisting of polyacrylic acid, polyacrylic acid salt, partially neutralized polyacrylic acid, carmellose sodium, polyvinyl alcohol, hydroxyethylcellulose, hydroxypropylcellulose, and carboxyvinyl polymer, the polyhydric alcohol is one or more polyhydric alcohols selected from the group consisting of propylene glycol, glycerin, D-sorbitol, and 1,3-butylene glycol, and the cross-linking agent is one or two cross-linking agents selected from the group consisting of aluminum glycinate and magnesium aluminometasilicate.

Another preferable embodiment of the present invention provides a patch, wherein the beraprost or a pharmacologically acceptable salt thereof is beraprost sodium, the water-soluble polymer is two or more water-soluble polymers selected from the group consisting of polyacrylic acid, polyacrylic acid salt, partially neutralized polyacrylic acid, carmellose sodium, polyvinyl alcohol, hydroxyethylcellulose, hydroxypropylcellulose, and carboxyvinyl polymer, the polyhydric alcohol is two or more polyhydric alcohols selected from the group consisting of propylene glycol, glycerin, D-sorbitol, and 1,3-butylene glycol, and the cross-linking agent is one cross-linking agent selected from the group consisting of aluminum glycinate and magnesium aluminometasilicate.

When water is added to the patch of the present invention, the amount of water may be 20 to 80% by weight, preferably 20 to 60% by weight, more preferably 30 to 46% by weight to the weight of a pasty preparation. When the amount of water is less than 20% by weight, the gel in the pasty preparation becomes too hard or does not become gel-like, and the pasty preparation cannot be easily spread on a backing. Meanwhile, the amount of water more than 80% by weight results in an insufficient gel formation and an insufficient adhesiveness of the patch.

In addition to the above ingredients, the patch of the present invention may comprise other ingredients such as a pH adjuster, a humectant, an excipient, a stabilizing agent, and a surfactant, if necessary.

Examples of the pH adjuster used in the patch of the present invention include acetic acid, formic acid, lactic acid, tartaric acid, oxalic acid, benzoic acid, glycolic acid, malic acid, citric acid, hydrochloric acid, nitric acid, sulfuric acid, sodium hydroxide, potassium hydroxide, methylamine, ethylamine, propylamine, dimethylamine, diethylamine, dipropylamine, trimethylamine, triethylamine, tripropylamine, monoethanolamine, monoethanolamine, monopropanolamine, dimethanolamine, diethanolamine, dipropanolamine, trimethanolamine, triethanolamine, and tripropanolamine. Especially, an organic acid such as acetic acid, formic acid, lactic acid, tartaric acid, oxalic acid, benzoic acid, glycolic acid, malic acid, and citric acid is preferable, and they may be used alone or in a combination of two or more of them.

Examples of the humectant used in the patch of the present invention include a saccharide such as sodium hyaluronate and a high-absorbent resin such as starch-acrylonitrile graft copolymer, starch-acrylic acid graft copolymer, starch-styrenesulfonic acid graft copolymer, starch-vinyl sulfonic acid graft copolymer, cross-linked polyvinyl alcohol, cross-linked polyethylene glycol diacrylate, and saponified acrylic acid-vinyl acetate copolymer. These humectants may be used alone or in a combination of two or more of them.

Examples of the excipient used in the patch of the present invention include kaolin, diatomaceous earth, hydrous silica, zinc oxide, anhydrous silicic acid, talc, titanium, bentonite, aluminum silicate, titanium oxide, aluminum metasilicate, magnesium silicate, light anhydrous silicic acid, calcium hydrogen phosphate, calcium sulfate, magnesium carbonate, and calcium phosphate. They may be used alone or in a combination of two or more of them.

Examples of the stabilizing agent used in the patch of the present invention include an edetate such as sodium edetate and trisodium ethylenediaminehydroxyethyl triacetate, sodium citrate, gluconic acid, a parahydroxybenzoate such as methyl parahydroxybenzoate and propyl parahydroxybenzoate, and tartaric acid. They may be used alone or in a combination of two or more of them.

Examples of the surfactant used in the patch of the present invention include polyoxyethylene sorbitan monooleate, sorbitan monooleate, glycerin fatty acid ester, polyglycerin fatty acid ester, sorbitan fatty acid ester, polyoxyethylene sorbitan fatty acid ester, polyoxyethylene sorbitol fatty acid ester, polyoxyethylene castor oil, polyoxyethylene hydrogenated castor oil, polyoxyethylene alkyl ether, alkyl ether carboxylate, alkanesulfonate, fatty acid monoglyceride sulfate, fatty acid amide amine salt, and benzethonium. They may be used alone or in a combination of two or more of them.

The backing used in the patch of the present invention is not limited to a specific backing, and may be an elastic or non-elastic backing. Examples of the backing include a film or a sheet composed of a synthetic resin such as polyethylene terephthalate, polyethylene, polypropylene, polybutadiene, ethylene-vinyl acetate copolymer, polyvinyl chloride, polyester, nylon, and polyurethane, or a laminate thereof, a porous membrane, a foam, a woven fabric, a non-woven fabric, and a paper material.

Examples of the release liner used in the patch of the present invention include a single material or a laminate composite material of a plastic film such as cast polypropylene, oriented polypropylene, polyethylene terephthalate, polybutylene terephthalate, polyethylene, polyester, polyurethane, and polystyrene, a paper, a synthetic paper, or a synthetic resin, and a laminate composite material of an aluminum foil or an evaporated film with the above material. The above single material or composite material may be siliconized or embossed, and further printed or colored.

The patch of the present invention may be an oily patch, an aqueous patch, or a non-aqueous patch, and an aqueous patch or a non-aqueous patch is especially preferable.

An aqueous patch of the present invention which comprises water can be prepared, for example, by the following process. Beraprost sodium is dissolved in a polyhydric alcohol to prepare a drug solution. Subsequently, a water-soluble polymer, a polyhydric alcohol, purified water, a cross-linking agent, and the other ingredients are sufficiently mixed and stirred to prepare an adhesive base. To the adhesive base is added the drug solution, and the mixture is sufficiently mixed to prepare an aqueous pasty preparation. The aqueous pasty preparation is evenly spread on a backing, then covered by a release liner, and cut into a desired size to prepare a patch of the present invention. The weight of the layer spread on the backing is not limited to a specific weight. The spread amount in an aqueous patch may be 200 to 2000 $g/m^2$, preferably 400 to 1500 $g/m^2$, more preferably 500 to 1000 $g/m^2$.

Meanwhile, a non-aqueous patch of the present invention which does not comprise water can be prepared, for example, by the following process. First, a water-soluble polymer is added to a polyhydric alcohol and dissolved therein by heating. After cooled, the obtained solution and a solution in which a cross-linking agent is dispersed in a polyhydric alcohol are mixed and stirred to prepare an adhesive base. Finally, to the adhesive base is added a drug solution in which beraprost sodium is dissolved in a polyhydric alcohol, and the mixture is homogeneously mixed to prepare a non-aqueous pasty preparation. The non-aqueous pasty preparation is spread on a backing, then covered by a release liner, and cut into a desired size to prepare a patch of the present invention. The spread amount of pasty preparation in the non-aqueous patch is 50 to 700 $g/m^2$, preferably 200 to 600 $g/m^2$, more preferably 300 to 500 $g/m^2$.

Hereinafter, the present invention is more specifically described by means of Examples. However, the present invention is not limited to the following Examples. Unless otherwise specified, the numerical values in Examples are shown by "% by weight".

EXAMPLES

Example 1

Beraprost sodium was dissolved in propylene glycol to prepare a drug solution. Subsequently, water-soluble polymers, glycerin, purified water, tartaric acid, aluminum glycinate, and the other ingredients were homogeneously mixed and stirred to prepare an adhesive base. Finally, to the adhesive base was added the drug solution, and the obtained solution was homogeneously mixed to prepare an aqueous pasty preparation. The aqueous pasty preparation was evenly spread on a backing in the spread amount of 500 g/m$^2$, then covered by a release liner, and cut into a desired size to prepare a patch (an aqueous patch) of the present invention. The amount of each ingredient is shown in Table 1.

Examples 2 to 12

The patch of each Example was prepared according to the ingredients shown in Table 1 to Table 3 and the process in Example 1.

Example 13

Polyacrylic acid and hydroxyethylcellulose were added to glycerin, and dissolved therein by heating. After cooled, to the obtained solution was added a solution in which magnesium aluminometasilicate was dispersed in propylene glycol, and the obtained solution was mixed and stirred to prepare an adhesive base. Finally, to the adhesive base was added a drug solution in which beraprost sodium was dissolved in propylene glycol, and the obtained solution was homogeneously mixed to prepare a non-aqueous pasty preparation. The non-aqueous pasty preparation was evenly spread on a backing in the spread amount of 500 g/m$^2$, then covered by a release liner, and cut into a desired size to prepare a patch (a non-aqueous patch) of the present invention. The amount of each ingredient is shown in Table 4.

TABLE 1

| Ingredient | Example 1 | Example 2 | Example 3 | Example 4 |
| --- | --- | --- | --- | --- |
| Beraprost sodium | 0.5 | 1.0 | 2.0 | 1.0 |
| Propylene glycol | 11 | 11 | 11 | 11 |
| Methyl parahydroxybenzoate | 0.1 | 0.1 | 0.1 | 0.1 |
| Propyl parahydroxybenzoate | 0.05 | 0.05 | 0.05 | 0.05 |
| Sodium edetate | 0.1 | 0.1 | 0.1 | 0.1 |
| Tartaric acid | 1 | 1 | 1 | 2 |
| Glycerin | 30 | 30 | 30 | 30 |
| Partially neutralized polyacrylic acid | 6 | 6 | 6 | 6 |
| Carmellose sodium | 4 | 4 | 4 | 4 |
| Polyacrylic acid aqueous solution (20%) | 20 | 20 | 20 | — |
| D-sorbitol solution (70%) | — | — | — | 20 |
| Polyvinyl alcohol | — | — | — | — |
| Carboxyvinyl polymer | — | — | — | — |
| Hydroxypropylcellulose | — | — | — | — |
| Kaolin | — | — | — | — |
| 1,3-Butylene glycol | — | — | — | — |
| Light anhydrous silicic acid | — | — | — | — |
| Polyoxyethylene sorbitan monooleate | — | — | — | — |
| Aluminum glycinate | 0.1 | 0.1 | 0.1 | 0.1 |
| Purified water | Appropriate amount | Appropriate amount | Appropriate amount | Appropriate amount |
| Total | 100 | 100 | 100 | 100 |

Unit: % by weight

TABLE 2

| Ingredient | Example 5 | Example 6 | Example 7 | Example 8 |
| --- | --- | --- | --- | --- |
| Beraprost sodium | 1.0 | 1.0 | 1.0 | 1.0 |
| Propylene glycol | 11 | 11 | 11 | 11 |
| Methyl parahydroxybenzoate | 0.1 | 0.1 | 0.1 | 0.1 |
| Propyl parahydroxybenzoate | 0.05 | 0.05 | 0.05 | 0.05 |

TABLE 2-continued

| Ingredient | Example 5 | Example 6 | Example 7 | Example 8 |
| --- | --- | --- | --- | --- |
| Sodium edetate | 0.1 | 0.1 | 0.1 | 0.1 |
| Tartaric acid | 2 | 1 | 2 | 1 |
| Glycerin | 30 | 30 | 30 | 30 |
| Partially neutralized polyacrylic acid | 6 | 6 | 6 | 6 |
| Carmellose sodium | 4 | 4 | 4 | 4 |
| Polyacrylic acid aqueous solution (20%) | — | — | — | 20 |
| D-sorbitol solution (70%) | — | — | 10 | — |
| Polyvinyl alcohol | 6.6 | — | 3.3 | — |
| Carboxyvinyl polymer | — | 1.5 | — | — |
| Hydroxypropylcellulose | — | — | — | 1 |
| Kaolin | — | — | — | — |
| 1,3-Butylene glycol | — | — | — | — |
| Light anhydrous silicic acid | — | — | — | — |
| Polyoxyethylene sorbitan monooleate | — | — | — | — |
| Aluminum glycinate | 0.1 | 0.1 | 0.1 | 0.1 |
| Purified water | Appropriate amount | Appropriate amount | Appropriate amount | Appropriate amount |
| Total | 100 | 100 | 100 | 100 |

Unit: % by weight

TABLE 3

| Ingredient | Example 9 | Example 10 | Example 11 | Example 12 |
| --- | --- | --- | --- | --- |
| Beraprost sodium | 1.0 | 1.0 | 1.0 | 1.0 |
| Propylene glycol | 11 | 11 | 11 | 11 |
| Methyl parahydroxybenzoate | 0.1 | 0.1 | 0.1 | 0.1 |
| Propyl parahydroxybenzoate | 0.05 | 0.05 | 0.05 | 0.05 |
| Sodium edetate | 0.1 | 0.1 | 0.1 | 0.1 |
| Tartaric acid | 1 | 1 | 1 | 1 |
| Glycerin | 30 | 15 | 30 | 30 |
| Partially neutralized polyacrylic acid | 6 | 6 | 6 | 6 |
| Carmellose sodium | 4 | 4 | 4 | 4 |
| Polyacrylic acid aqueous solution (20%) | 20 | 20 | 20 | 20 |
| D-sorbitol solution (70%) | — | — | — | — |
| Polyvinyl alcohol | — | — | — | — |
| Carboxyvinyl polymer | — | — | — | — |
| Hydroxypropylcellulose | — | — | — | — |
| Kaolin | 3 | — | — | — |
| 1,3-Butylene glycol | — | 15 | — | — |
| Light anhydrous silicic acid | — | — | 2 | — |
| Polyoxyethylene sorbitan monooleate | — | — | — | 0.2 |
| Aluminum glycinate | 0.1 | 0.1 | 0.1 | 0.1 |
| Purified water | Appropriate amount | Appropriate amount | Appropriate amount | Appropriate amount |
| Total | 100 | 100 | 100 | 100 |

Unit: % by weight

TABLE 4

| Ingredient | Example 13 |
| --- | --- |
| Beraprost sodium | 1.0 |
| Propylene glycol | 17.5 |
| Glycerin | 70 |
| Hydroxyethylcellulose | 2 |
| Magnesium aluminometasilicate | 2.5 |
| Polyacrylic acid | 7 |
| Total | 100 |

Unit: % by weight

COMPARATIVE EXAMPLES

Comparative Example 1

Beraprost sodium was dissolved in methanol, and then to the obtained solution was added ethyl acetate to prepare a drug solution. An adhesive solution, which was prepared by homogeneously mixing and stirring the drug solution and an acrylic adhesive (Duro-Tak 87-2516), was spread on a release liner. After ethyl acetate was removed by drying to prepare an adhesive layer having the thickness of 50 μm, a backing was applied to the layer to prepare a tape formulation. The amount of each ingredient is shown in Table 5.

Comparative Example 2

Beraprost in free form was dissolved in ethyl acetate to prepare a drug solution. The drug solution and an acrylic adhesive (Duro-Tak 87-2516) were homogeneously mixed and stirred to prepare an adhesive solution, and then the solution was spread on a release liner. After the solvent was removed by drying to prepare an adhesive layer having the thickness of 50 μm, a backing was applied to the layer to prepare a tape formulation. The amount of each ingredient is shown in Table 5.

Comparative Example 3

A patch was prepared according to the amount of each ingredient and process in Example 1 disclosed in Patent Document 2. The amount of each ingredient is shown in Table 5.

TABLE 5

| Ingredient | Comparative Example 1 | Comparative Example 2 | Comparative Example 3 |
| --- | --- | --- | --- |
| Beraprost sodium | 2.0 | — | 2.0 |
| Beraprost in free form | — | 1.9 | — |
| Duro-Tak 87-2516 | 98.0 | 98.1 | — |
| Myristyl alcohol | — | — | 5.0 |
| Ammonium chloride | — | — | 0.25 |
| Styrene-isoprene-styrene block copolymer (SIS) | — | — | 24.41 |
| Arkon P-100 | — | — | 43.93 |
| Liquid paraffin | — | — | 24.41 |
| Total | 100 | 100 | 100 |

Unit: % by weight

TEST EXAMPLES

Test Example 1

In Vitro Hairless Rat Skin Permeability Test

In order to study the transdermal absorbability of beraprost in the patch of the present invention, in vitro skin permeability test in a hairless rat was carried out on each formulation of Examples and Comparative Examples 1 and 2. An excised abdominal skin of a male hairless rat (HWY series, 7 weeks old) was put in a Franz diffusion cell, and each test formulation cut into a round shape (Φ 14 mm) was applied thereto. The receptor side was filled with phosphate buffered saline, and hot water of 37° C. was circulated in the water jacket. The receptor solution was sampled with lapse of time, and the amount of beraprost permeated the skin was measured by a liquid chromatography. Each cumulative amount of permeated drug after 24 hours from the start of the test was calculated from the measured amount. The results are shown in Table 6.

TABLE 6

| Example/ Comparative Example | Beraprost sodium or beraprost in free form (% by weight) | Cumulative amount of permeated drug after 24 hours ($\mu g/cm^2$) |
| --- | --- | --- |
| Example 1 | 0.5 (Beraprost sodium) | 7.8 |
| Example 2 | 1.0 (Beraprost sodium) | 10.3 |
| Example 3 | 2.0 (Beraprost sodium) | 12.1 |
| Example 4 | 1.0 (Beraprost sodium) | 13.2 |
| Example 5 | 1.0 (Beraprost sodium) | 12.9 |
| Example 6 | 1.0 (Beraprost sodium) | 8.7 |
| Example 7 | 1.0 (Beraprost sodium) | 5.6 |
| Example 8 | 1.0 (Beraprost sodium) | 3.6 |
| Example 9 | 1.0 (Beraprost sodium) | 8.7 |
| Example 10 | 1.0 (Beraprost sodium) | 2.5 |
| Example 11 | 1.0 (Beraprost sodium) | 9.6 |
| Example 12 | 1.0 (Beraprost sodium) | 9.2 |
| Example 13 | 1.0 (Beraprost sodium) | 4.2 |
| Comparative Example 1 | 2.0 (Beraprost sodium) | 0.1 |
| Comparative Example 2 | 1.9 (Beraprost in free form) | 2.1 |

Test Example 2

Formulation Property Test

The formulation properties of each Example formulation and each Comparative Example formulation were evaluated in (1) cohesive power, (2) finger tack, and (3) applicability and (4) adhesive deposit when actually applied to a skin. Each test was carried out according to the following methods.

(1) Cohesive power: a pasty preparation surface was pressed with a finger, and then the condition of the pasty preparation on the formulation surface was visually observed after the release of the finger.

(2) Finger tack: a pasty preparation surface was pressed with a finger, and then the adhesiveness at the release of the finger was evaluated.

(3) Applicability: each formulation was applied to a skin, and the presence or absence of a condition such as floating and peeling of the formulation during application was visually observed.

(4) Adhesive deposit: each formulation was applied to a skin for a period of time and then peeled off, and the presence or absence of the pasty preparation remaining on the skin surface was visually observed.

Regarding each evaluation item, an excellent result is indicated by the "∘" mark, a slightly poor result is indicated by the "Δ" mark, and a poor result is indicated by the "x" mark. The results are shown in Table 7.

TABLE 7

| | (1) Cohesive power | (2) Finger tack | (3) Applicability | (4) Adhesive deposit |
|---|---|---|---|---|
| Example 1 | ○ | ○ | ○ | ○ |
| Example 2 | ○ | ○ | ○ | ○ |
| Example 3 | ○ | ○ | ○ | ○ |
| Example 4 | ○ | ○ | ○ | ○ |
| Example 5 | ○ | ○ | ○ | ○ |
| Example 6 | ○ | Δ | Δ | ○ |
| Example 7 | ○ | ○ | ○ | ○ |
| Example 8 | ○ | ○ | ○ | ○ |
| Example 9 | ○ | ○ | ○ | ○ |
| Example 10 | ○ | ○ | ○ | ○ |
| Example 11 | ○ | ○ | ○ | ○ |
| Example 12 | ○ | ○ | ○ | ○ |
| Example 13 | ○ | Δ | Δ | ○ |
| Comparative Example 1 | ○ | ○ | ○ | ○ |
| Comparative Example 2 | ○ | ○ | ○ | ○ |
| Comparative Example 3 | ○ | x | x | ○ |

The above test results demonstrate that each patch of Comparative Examples 1 and 2 only achieves low transdermal absorption of beraprost or a pharmacologically acceptable salt thereof. Also, the above test results demonstrate that the oily patch of Comparative Example 3, which comprises ingredients such as an absorption enhancer in order to enhance the transdermal absorption of said drug, does not have desired formulation properties as a patch. Meanwhile, the above test results demonstrate that each patch of the present invention achieves higher transdermal absorption of said drug as compared to each patch of Comparative Examples 1 and 2, and has very excellent formulation properties as compared to the patch of Comparative Example 3. Namely, the patch of the present invention achieves high transdermal absorption of said drug and has very excellent formulation properties.

INDUSTRIAL APPLICABILITY

The present invention can provide a patch which achieves high transdermal absorption of beraprost or a pharmacologically acceptable salt thereof and has excellent formulation properties. Further, the present invention can provide a patch which has a low risk of side effect by stably maintaining the blood level of said drug without a rapid elevation and also has low skin irritation.

The invention claimed is:

1. A patch comprising a pasty preparation consisting of beraprost or a pharmacologically acceptable salt thereof, a water-soluble polymer, a polyhydric alcohol, a cross-linking agent, and, optionally, one or more ingredients selected from the group consisting of:

one or more pH adjusters selected from the group consisting of acetic acid, formic acid, lactic acid, tartaric acid, oxalic acid, benzoic acid, glycolic acid, malic acid, citric acid, hydrochloric acid, nitric acid, sulfuric acid, sodium hydroxide, potassium hydroxide, methylamine, ethylamine, propylamine, dimethylamine, diethylamine, dipropylamine, trimethylamine, triethylamine, tripropylamine, monomethanolamine, monoethanolamine, monopropanolamine, dimethanolamine, diethanolamine, dipropanolamine, trimethanolamine, triethanolamine, and tripropanolamine;

one or more humectants selected from the group consisting of a saccharide and a high-absorbent resin;

one or more excipients selected from the group consisting of kaolin, diatomaceous earth, hydrous silica, zinc oxide, anhydrous silicic acid, talc, titanium, bentonite, aluminum silicate, titanium oxide, aluminum metasilicate, magnesium silicate, light anhydrous silicic acid, calcium hydrogen phosphate, calcium sulfate, magnesium carbonate, and calcium phosphate;

one or more stabilizing agents selected from the group consisting of an edetate, sodium citrate, gluconic acid, a parahydroxybenzoate, and tartaric acid;

one or more surfactants selected from the group consisting of polyoxyethylene sorbitan monooleate, sorbitan monooleate, glycerin fatty acid ester, polyglycerin fatty acid ester, sorbitan fatty acid ester, polyoxyethylene sorbitan fatty acid ester, polyoxyethylene sorbitol fatty acid ester, polyoxyethylene castor oil, polyoxyethylene hydrogenated castor oil, polyoxyethylene alkyl ether, alkyl ether carboxylate, alkanesulfonate, fatty acid monoglyceride sulfate, fatty acid amide amine salt, and benzethonium; and water.

2. The patch according to claim 1, consisting of 0.01 to 10% by weight of the beraprost or a pharmacologically acceptable salt thereof, 1 to 30% by weight of the water-soluble polymer, 5 to 95% by weight of the polyhydric alcohol, and 0.01 to 5% by weight of the cross-linking agent to the weight of the pasty preparation.

3. The patch according to claim 1, wherein the beraprost or a pharmacologically acceptable salt thereof is beraprost sodium.

4. The patch according to claim 1, wherein the water-soluble polymer is one or more water-soluble polymers selected from the group consisting of polyacrylic acid, polyacrylic acid salt, partially neutralized polyacrylic acid, carmellose sodium, polyvinyl alcohol, hydroxyethylcellulose, hydroxypropylcellulose, and carboxyvinyl polymer.

5. The patch according to claim 1, wherein the polyhydric alcohol is one or more polyhydric alcohols selected from the group consisting of propylene glycol, glycerin, D-sorbitol, and 1,3-butylene glycol.

6. The patch according to claim 1, wherein the cross-linking agent is one or two cross-linking agents selected from the group consisting of aluminum glycinate and magnesium aluminometasilicate.

* * * * *